(12) United States Patent
Yakel et al.

(10) Patent No.: US 9,084,593 B2
(45) Date of Patent: Jul. 21, 2015

(54) HOLDING APPARATUS FOR MEDICAL IMPLEMENTS

(75) Inventors: Lindsay S. Yakel, Chicago, IL (US);
Kimberly M. Haines, Deerdfield, IL (US); Alan W. Dye, Mundelein, IL (US); Michael S. McMahon, Libertyville, IL (US)

(73) Assignee: Medline Industries, Inc., Mundelein, IL (US)

( * ) Notice: Subject to any disclaimer, the term of this patent is extended or adjusted under 35 U.S.C. 154(b) by 893 days.

(21) Appl. No.: 12/647,508

(22) Filed: Dec. 27, 2009

(65) Prior Publication Data

US 2011/0155599 A1 Jun. 30, 2011

(51) Int. Cl.
*B65D 83/10* (2006.01)
*A61B 19/02* (2006.01)

(52) U.S. Cl.
CPC ......... *A61B 19/0271* (2013.01); *A61B 19/0256* (2013.01); *A61B 19/0288* (2013.01); *A61B 2019/0211* (2013.01)

(58) Field of Classification Search
USPC .................. 206/364, 365, 366, 370, 382, 562
See application file for complete search history.

(56) References Cited

U.S. PATENT DOCUMENTS 4,333,567 A * 6/1982 Leonard .................. 206/368
4,767,008 A * 8/1988 Warnecke et al. ......... 206/570
5,024,326 A 6/1991 Sandel et al.
5,035,703 A 7/1991 Baskas
5,078,695 A 1/1992 Farrar, Jr. et al.
6,955,259 B1 * 10/2005 Jesse .............................. 206/366
7,240,798 B1 * 7/2007 Chiang ......................... 206/562
7,407,054 B2 * 8/2008 Seiler et al. ................... 206/370
2005/0268505 A1 12/2005 Sandel et al.

OTHER PUBLICATIONS

"Medline Catalog", Blood Smaple/Needle Transport Systems by Hopkins Medical; Item No. H-M661983; Publication date unknown but believed to be prior to present application.
"Medline Brochure", Diagnostic Cardiology: For your Procedural Needs; pp. 1-36; Publication Date unknown but believed to be prior to present application.
"Medline Brochure", Minor Procedure Trays: Delivering Quality, Convenience and Efficiency; pp. 1-60; Publication Date unknown but believed to be prior to present application.

(Continued)

*Primary Examiner* — Anthony Stashick
*Assistant Examiner* — Raven Collins
(74) *Attorney, Agent, or Firm* — Philip H. Burrus, IV

(57) ABSTRACT

A holder (100) for medical implements includes a base member (101) and at least one medical implement receiver (110). Each medical implement receiver (110) includes a pair of retention members (114,115) extending from the base member (101). Opposing faces (116,117) of the retention members (114,115) define an implement receiving recess (118). Slots (120,121) are provided in the opposing faces (116,117) to facilitate reception of syringe needle cap rims (330). The holder (100) can be configured as a medical tray (801) that can be attached to one or more other medical trays, including one having cup holders (870,871,872), one including a needle containment receptacle (881), or other medical trays.

11 Claims, 7 Drawing Sheets

(56) References Cited

OTHER PUBLICATIONS

"Medline Brochure", OR Necessities: Separate Sterile Pack Components; pp. 1-36; Publication Date unknown but believed to be prior to present application.

"Medline Catalog", Quinke Spinal Trays by Beckton Dickinson; Product No. BD405609,H; B-D405611-12; B-D405621-23;B-D405636; B-D405735; B-D406064; Publication Date unknown but believed to be prior to present application.

"Medline Catalog", SharpStop Needle Boxes by DeRoyal; Item No. QTX77400114; Publication Date Unknown but believed to be prior to present application.

"Medline Catalog", VanishPoint Allergy Syringe Trays by Retractable Tech; Product No. RTI10134CS; Publication Date Unknown but believed to be prior to present application.

"Medline Catalog", Whitacre Spinal Trays by Becton Dickinson; Product ID B-D405706 and B-D405709; Publication Date Unknown but believed to be prior to present application.

* cited by examiner

HOLDING APPARATUS FOR MEDICAL IMPLEMENTS

BACKGROUND

1. Technical Field

This invention relates generally to a holder for medical devices, and more particularly to a holder employing one or more medical implement receivers configured to hold both syringe caps and other devices, such as scalpels.

2. Background Art

Surgeons and other medical professionals use a wide variety of tools, implements, and devices when performing medical procedures. For example, in even the most routine surgery, a surgeon may employ multiple scalpels for cutting, needles for suturing, and syringes for injecting medications into drip bags, as well as specialized tools associated with a particular procedure. Nurses and other medical professionals are sometimes tasked with organizing the various implements. This is frequently accomplished by spreading the tools and implements in a loose fashion across a tray. The nurse may additionally be asked to hand each device to a doctor.

One problem associated with this organizational arrangement involves the sharp edges associated with many medical implements. For example, scalpels have razor sharp edges designed to cut skin. Similarly, syringes have hypodermic needles attached that are designed to pierce skin. When preparing for surgery, some medical professionals will remove all protective coverings so that the implements are ready for use. The coverings may be left off during the procedure so that the tool or implement may be used multiple times. This presents a risk that the medical professional will be inadvertently injured when grasping for the implement, as medical professionals need to be able to quickly access these implements so that they are ready exactly when needed. Additionally, there is a risk that one of the medical professionals will be inadvertently injured when the implement is handed to another person.

There is thus a need for a holder for these medical implements that can be used for both organization and to help prevent inadvertent injury.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
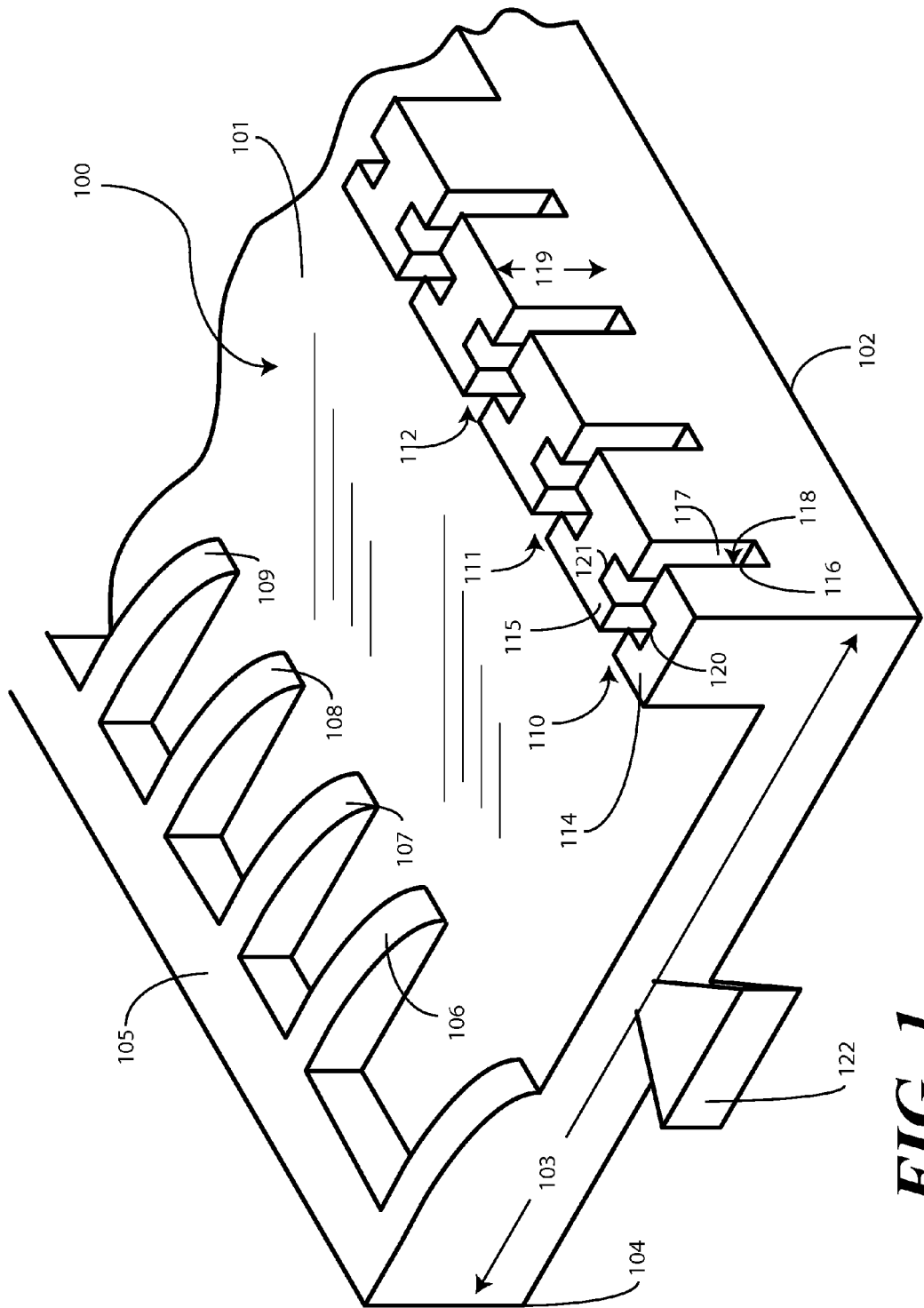
FIG. 1 illustrates a perspective view of one holder configured as a medical tray in accordance with embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Embodiments of the present invention provide various arrangements of medical trays and holders for retaining medical implements. For example, in one embodiment a medical implement holder is configured as a tray having a base member and one or more medical implement receivers configured to hold scalpels and other thin medical implements. In one embodiment, each medical implement receiver includes two retention members having slots cut into their faces. When configured in this fashion, the medical implement receivers are configured to receive syringe needle caps, with the syringe needle cap rim fitting into the slot cuts. Where a syringe having the syringe needle cap attached thereto is inserted into these retention members, the retention members permit a medical professional to remove and attach the syringe needle cap to a Luer fitting or slip-tip fitting using only one hand. Further, the retention members hold the syringe in an organized and easily accessible manner when the needle is inserted into the needle cap.

The trays and holders described herein can be integrated with, or attached to, other medical trays. For example, in one embodiment a tray or holder can be attached to another tray configured with cup holders. Further, the cup holders and medical implement receivers can be color coded as well. Where a syringe having a syringe needle cap disposed in a pair of retention members is to be used with a cup of medication seated within the cup holders, color-coding provides the medical professional with a simple and accurate visual method for ensuring the proper syringe withdraws the proper medication.

In another embodiment, a tray or holder can be attached to a needle containment receptacle, a scalpel blade remover, or combinations thereof. When configured in this manner, a medical professional can easily dispose of sharp objects such as blades and hypodermic needles when no longer needed.

For example, scalpels and syringes having syringe needle caps can rest in the tray or holder when in use. Once these devices are no longer needed, the medical professional can prepare these sharp objects for disposal by transferring them to the attached sharp object receptacle.

Figure 2:
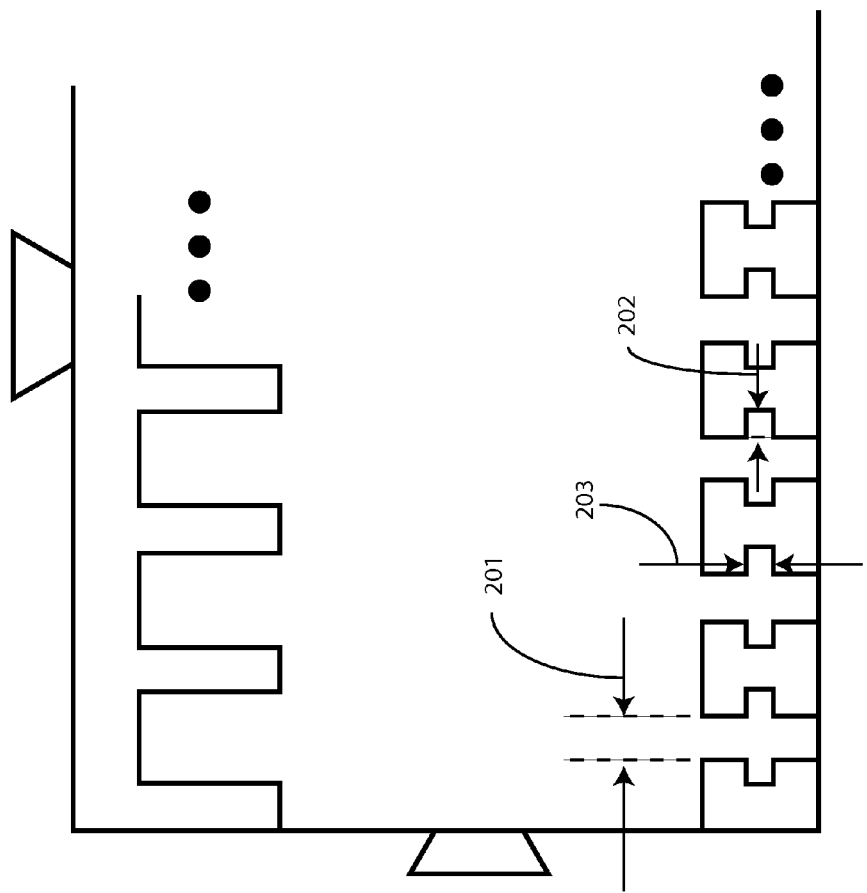
FIG. 2 illustrates a plan view of one holder configured as a medical tray in accordance with embodiments of the invention.

Turning now to FIGS. 1 and 2, illustrated therein is one embodiment of a holder 100 for medical implements in accordance with embodiments of the invention. FIG. 1 illustrates a perspective view of the holder 100, while FIG. 2 illustrates a top, plan view of the holder 100.

The holder 100 of FIG. 1 is configured as a tray, having a base member 101 that runs from a first side 102 across a length 103 of the base member 101 to a distal second side 104. While the length 103 can vary based upon application, in one embodiment the length 103 is between 60 millimeters and 110 millimeters.

The holder 100 can be manufactured in a variety of ways. In one embodiment, the holder 100 is manufactured from a thermoplastic material by way of an injection molding process or from a sheet of thermoplastic material in a vacuum molding process. As will be shown below, in one embodiment portions of the holder 100 are configured to be flexible or pliant to "grip" medical implements inserted therein. Some materials suitable for such constructions include styrene, resins, rubber, or other pliant compounds. In other embodiments, materials such as acrylonitrile butadiene styrene (ABS), polycarbonate (PC) and polycarbonate-ABS can be used. It will be clear to those of ordinary skill in the art having the benefit of this disclosure that other materials and manufacturing methods can be used.

A mechanical stop wall 105 is present on the second side 104. The mechanical stop wall 105 of FIG. 1 is configured as a raised rim that extends upwardly from the base member 101 and passes along an edge of the second side 104. While this is one illustrative embodiment, others could be similarly constructed. For example, the mechanical stop wall 105 need not be on the edge of the second side 104. Material from the base member 101 may extend past the mechanical stop wall 105 in some embodiments, such as where the holder 100 is to be coupled to other holders as will be explained below.

In the illustrative embodiment of FIG. 1, the mechanical stop wall 105 includes one or more separating walls 106,107, 108,109 that extend outwardly from the mechanical stop wall 105 towards the first side 102 of the holder 100. As will be shown below, in one embodiment were medical implements are placed within the holder 100, end portions of these medical implements may rest against, or near to, the mechanical stop wall 105. Where this is the case, the one or more separating walls 106,107,108,109 prevent those implements from becoming askew within the holder 100 or touching other implements by providing partial barriers therebetween. The illustrative one or more separating walls 106,107,108,109 of FIG. 1 extend along a portion of the length 103 of the base member 101. However, other embodiments are possible, such as those where the one or more separating walls extend across a larger portion or all of the length 103. Additionally, some embodiments may not include the one or more separating walls 106,107,108,109 at all.

The holder 100 also includes at least one medical implement receiver. In the illustrative embodiment of FIG. 1, three medical implement receivers 110,111,112 are shown. It will be clear to those of ordinary skill in the art having the benefit of this disclosure that any number of medical implement receivers can be used. For example, the width 113 of the base member 101 can be extended to accommodate four, five, or six, or even ten, twelve, or more medical implement receivers.

Each medical implement receiver 110,111,112 includes a pair of retention members 114,115 extending upwardly from the first side 102 of the base member 101. As with the location of the mechanical stop wall 105, the location of the medical implement receivers 110,111,112 can be in any of a variety of locations. In the illustrative embodiment of FIG. 1, they are located along an edge of the first side 102 of the base member 101. However, the base member 101 may extend in the direction of the length 103 past the medical implement receivers 110,111,112 to provide under-support for medical implements placed within the holder 100.

The retention members 114,115 can be configured in different ways. For example, retention member 114 is configured as a single end retention member, serving to receive implements in medical implement receiver 110. Retention member 115 is configured as a double sided retention member, serving to receive implements both in medical implement receiver 110 and medical implement receiver 111. In one embodiment, the height 119 of the retention members 114, 115 is between 0.75 centimeters and 1.5 centimeters. Other heights may also be used.

Opposing faces 116,117 of the retention members 114,115 define an implement receiving recess 118. As will be shown in FIG. 3, medical implements such as scalpels syringe tips, Luer connection fittings, slip-tip fittings, and syringe needle caps can be inserted into the implement receiving recess 118. The opposing faces 116,117 can be various distances apart from each other. For example, they can be separated by a width 201 of between 1.27 millimeters and 8.89 millimeters. In one embodiment, the implement receiving recess 118 has a width 201 of about 8 millimeters.

Each opposing face 116,117 includes a slot 120,121. The slot 120,121 is a cut into each opposing face 116,117 and extends into each retention member 114,115 from the opposing faces 116,117. In one embodiment, the slots 120,121 extend into each retention member 114,115 substantially orthogonally relative to the implement receiving recess 118, with each slot 120,121 being approximately rectangular in shape. In such a configuration, the plan cross section of retention member 114 becomes roughly a C-shape or sideways U-shape, while the plan cross section of retention member 115 becomes an I-shape or sideways H-shape. It will be clear to those of ordinary skill in the art having the benefit of this disclosure that other configurations are possible as well. For example, rather than being rectangular in shape, the slots 120,121 can be triangular or take other shapes.

In one embodiment, the dimensions of the slots 120,121 are configured such that a portion of a needle cap rim of a syringe. Experimental testing has shown that suitable dimensions range from 0.75 millimeters to 1.0 millimeters, although these dimensions can be extended. In one embodiment, each slot 120,121 has a width 202 of 1 millimeter and a length 203 of 1 millimeter.

While the term "retention member" is used herein, in some embodiments the retention members 114,115 will physically retain implements inserted in the medical implement receivers 110,111,112. For example, in one embodiment, the opposing faces 116,117 are configured to be pliable or flexible by way of the material that is selected for their construction and the thickness selected for their corresponding structures. In such an embodiment, each opposing face 116,117 forms a cantilevered surface as it is fixed to the base member 101. Thus, the opposing faces 116,117 can slightly flex when medical implements having diameters greater than the width 201 of the implement receiving recess 118 are inserted therein. However, where medical implements having a diameter that is less than the width 201 of the implement receiving recess 118, or where the opposing faces 116,117 are not constructed to be pliable, there may be little or no actual "retention" in the medical implement receivers. For consistency and ease of description, the term "retention members" is used to refer to both embodiments, unless otherwise noted.

In one embodiment, the holder 100 includes an optional mechanical connector 122 for coupling to other holders or other medical containment devices, containers, or trays. In the illustrative embodiment of FIG. 1, the mechanical connector 122 is shown as being a male mating connector. However, it will be clear to those of ordinary skill in the art having the benefit of this disclosure that embodiments of the invention are not so limited.

The mechanical connector 122 can be configured in other ways. Adhesives or double-sided tape can serve as the mechanical connector 122. Similarly, a hook and loop fastener or other fasteners can serve as the mechanical connector 122. In one embodiment where a mechanical connector 122 is included, the holder 100 is configured to be selectively detachable from other components. Such would be the case with the male mating connector of FIG. 1.

In other embodiments, the holder 100 may be permanently affixed to other components. For example, FIG. 7 will illustrate a medical tray (702) configured as a cup holder attached to a medical tray (701) comprising medical implement receivers. This system could be permanently coupled together during the molding process, or alternatively may be selectively detachable using one of the mechanical connectors described above.

Figure 3:
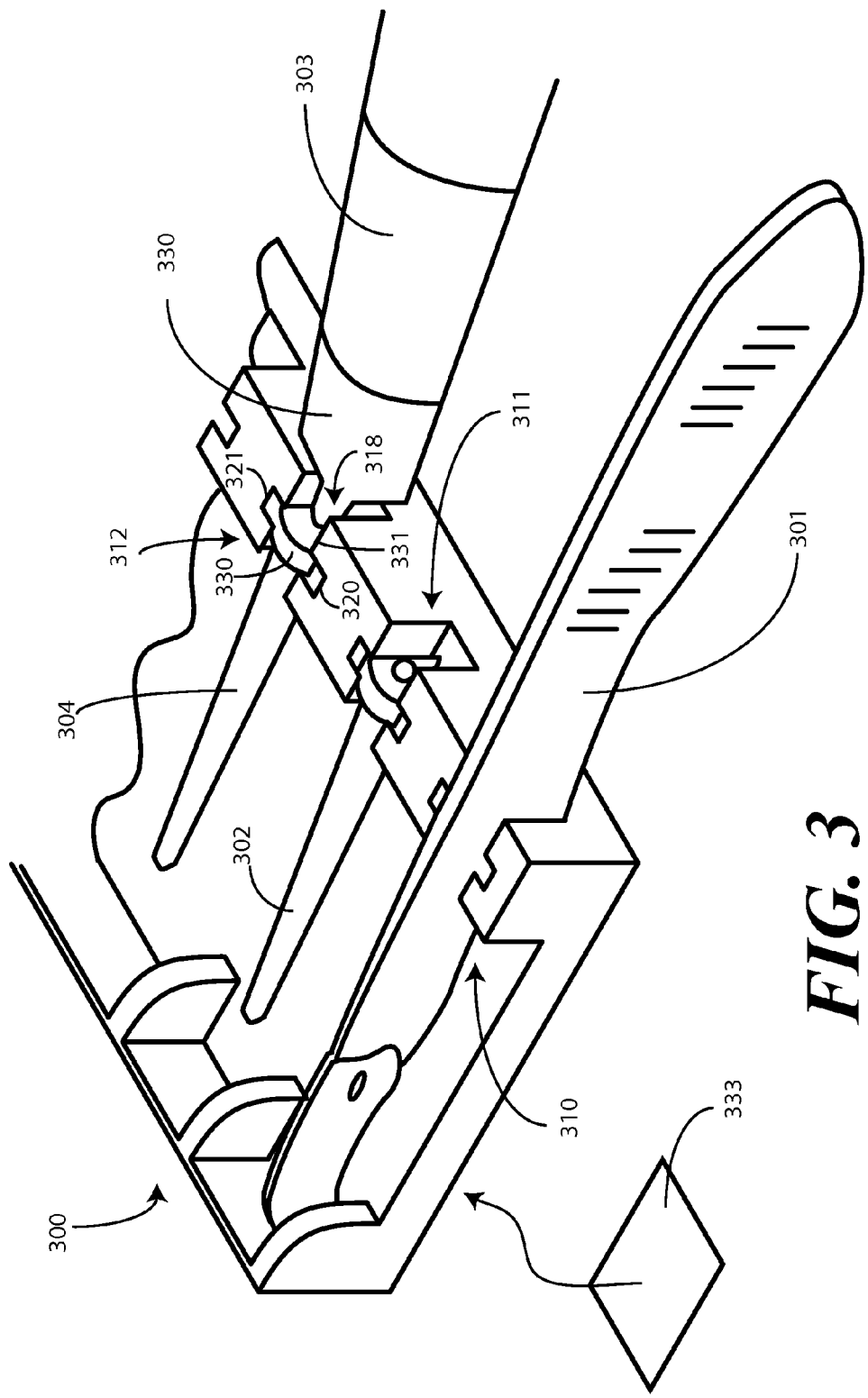
FIG. 3 illustrates one embodiment of a holder having a scalpel, syringe needle cap, and syringe and syringe needle cap assembly in accordance with embodiments of the invention.

Turning now to FIG. 3, illustrated therein is an exemplary holder 300 having medical implements inserted therein in accordance with embodiments of the invention. Specifically, a scalpel 301, syringe needle cap 302, syringe 303 and syringe needle cap 304 combination have been inserted into medical implement receivers 310,311,312. The illustration of FIG. 3 shows how the slots 320,321 can be used to facilitate removal or attachment of the syringe needle cap 304 from a Luer connection 330 of the syringe 303. Note that slip-tip fittings may be substituted for the Luer connection 330 as well.

When syringes 303 having syringe needle caps 304 are inserted into a medical implement receiving recess 318 of a medical implement receiver 312, in one embodiment the rim 330 of the syringe needle cap 304 is configured to fit within the slots 320,321. In one embodiment, a face portion 331 extending from each slot 320 towards an edge of the holder 300 has a length configured to fit between the syringe needle cap rim 330 and a Luer fitting 332 of the syringe.

In such a configuration, a medical services professional can insert the syringe needle cap rim 330 into the slots 320,321 and draw the syringe 303 away from the holder 300, thereby releasing the syringe needle cap 304 from the Luer fitting 332. Similarly, the medical services professional can align the needle of the syringe 303 with the syringe needle cap 304 and push the syringe 303 towards the holder 300 to re-apply the syringe needle cap 304 to the Luer fitting 332. As will be understood by those of ordinary skill in the art, the holder 300 of FIG. 3 allows one-handed removal and reattachment of the syringe needle cap 304. This offers an advantage over prior art systems where needles are generally left uncovered in that the medical services professional can help ensure that no one is inadvertently injured by the needle without having to use two hands to reattach the syringe needle cap 304.

When the implement receiving recess 308 is configured to receive syringe needle caps 304, scalpels 301 may also be placed into the medical implement receivers 310. As syringe needle caps 304 are often thicker than scalpels 301, the scalpels 301 will generally rest loosely within the implement receiving recesses 318. However, this configuration can still be desirable in that the scalpel 301 is held upright for quick and easy accessibility. Note that the implement receiving recesses 318 can be configured with different widths, with some designed for scalpels 301 and others being designed for syringes 303 or syringe needle caps 302,304.

In one embodiment, an adhesive patch 333 or adhesive strip may be attached to the bottom of the tray 300. Such an adhesive patch 333 can be used to selectively adhere the tray 300 to a surgical drape on a Mayo stand, or to a stand or table, to prevent slippage while in use.

Figure 4:
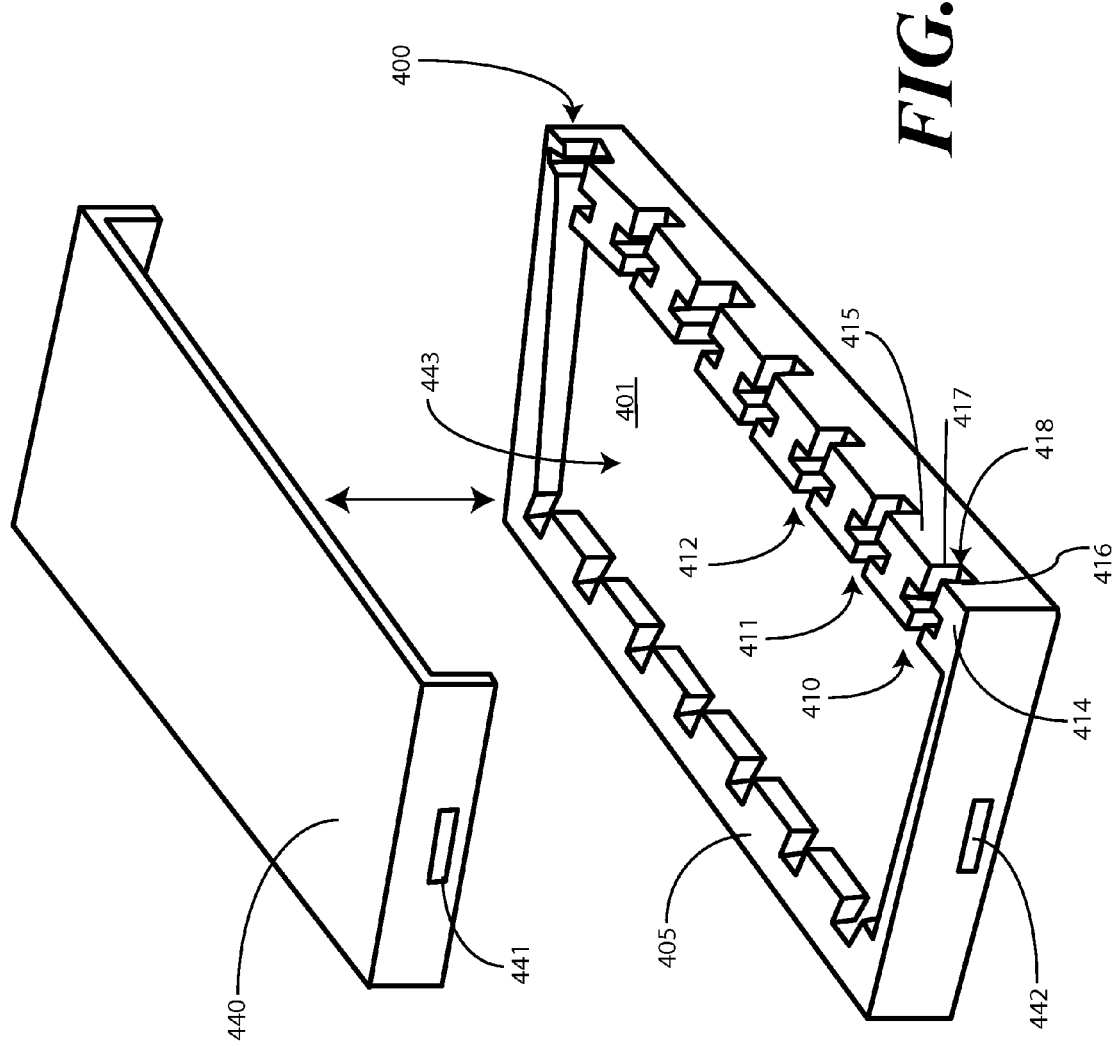
FIG. 4 illustrates one medical tray having a detachable lid in accordance with embodiments of the invention.

Turning now to FIG. 4, illustrated therein is one embodiment of a medical tray 400 configured to hold medical implements such as syringes and scalpels in accordance with embodiments of the invention. Many elements of the medical tray 400 are similar to the holder (100) of FIGS. 1 and 2. For example, a base member 401 has a raised rim 405 passing about at least a portion of the base member 401. The raised rim 405, which passes about three sides of the base member 401 in the illustrative embodiment of FIG. 4, serves as a mechanical stop wall for implements placed within the medical tray 400.

Also as in FIGS. 1 and 2, one or more medical implement receivers 410,411,412 extend from the base member 401, with each medical implement receiver 410,411,412 comprising a pair of retention members 414,415 having opposing faces 416,417 that define an implement receiving recess 418. Each opposing face 416,417 has a slot extending into each retention member 414,415 for receiving syringe cap needle rims.

In the embodiment of FIG. 4, a lid 440 is provided to cover an area 443 disposed between the raised rim and the medical implement receivers 410,411,412. The lid 440 offers an additional layer of security in that it prevents medical services professionals from inadvertently touching sharp portions of medical implements inserted into the medical implement receivers 410,411,412.

In FIG. 4, the lid 440 is selectively detachable from the medical tray 400 by way of a mechanical connector. The illustrative mechanical connector shown includes a tab 441 on the lid 440 and a detent 442 on the medical tray 400. Other connectors may also be used.

In one embodiment, the lid 440 is configured to be pellucid or transparent, so that the medical services provider can visually inspect the contents of the medical tray 400. Additionally, selective printing or engraving can be included on the lid, such as color coding or medical implement usage or disposal instructions.

Figure 5:
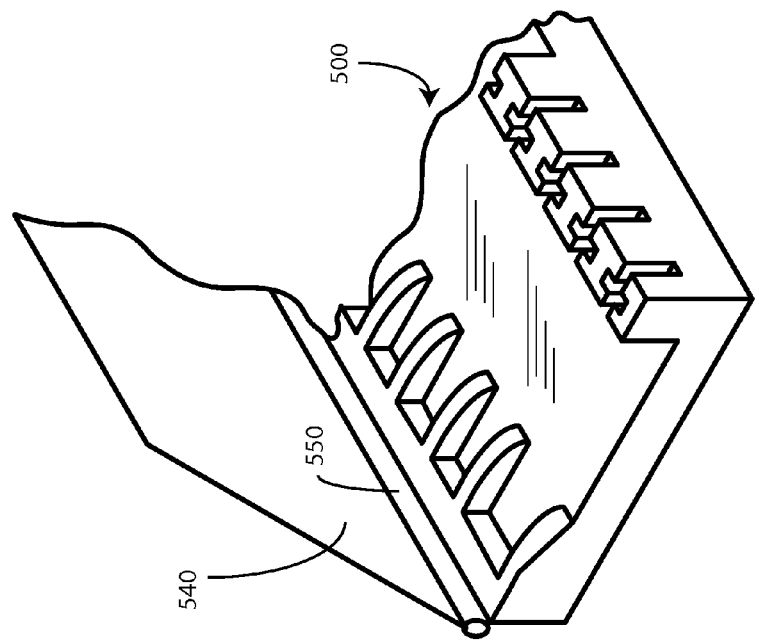
FIG. 5 illustrates one medical tray having a hinged lid in accordance with embodiments of the invention.

Turning now to FIG. 5, illustrated therein is an alternate configuration for a medical tray 500 configured to hold medical implements such as scalpels or syringes having a lid 540 coupled thereto. Rather than being selectively detachable from the tray as was the case in FIG. 4, the lid 540 of FIG. 5 is coupled to the tray 500 by way of a hinge 550. In this configuration, the medical services provider can quickly and easily access contents disposed within the tray 500 if necessary, without having to find additional work surface space for a detachable lid. It will be clear to those of ordinary skill in the art having the benefit of this disclosure that other tray/lid interfaces beyond the mechanical connector of FIG. 4 and the hinge of FIG. 5 may also be used without departing from the spirit and scope of the invention.

Figure 6:
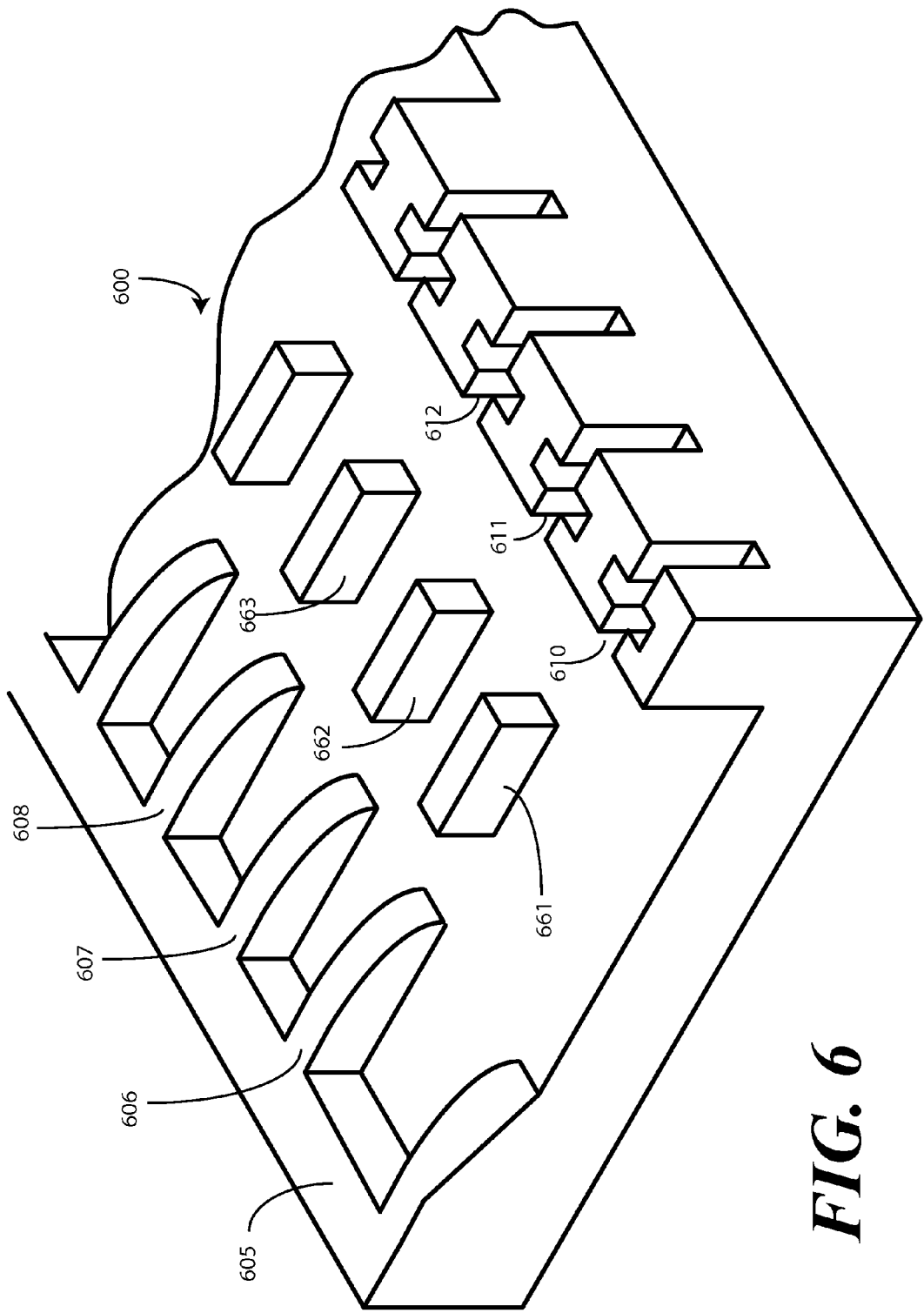
FIG. 6 illustrates an alternate embodiment of a holder configured as a medical tray in accordance with embodiments of the invention.

Turning now to FIG. 6, illustrated therein is an alternate holder 600 configured to receive medical implements in accordance with embodiments of the invention. The holder 600 of FIG. 6 includes one or more separation baffles 661, 662,663 disposed between a mechanical stop wall 605 and the medical implement receivers 610,611,612. The separation baffles 661,662,663 help to further ensure that medical implements inserted into the holder 600 do not touch each other. Note also that in the embodiment of FIG. 6, the separating walls 606,607,608 have been extended in width when compared to those of FIGS. 1 and 2 to provide additional stability.

Figure 7:
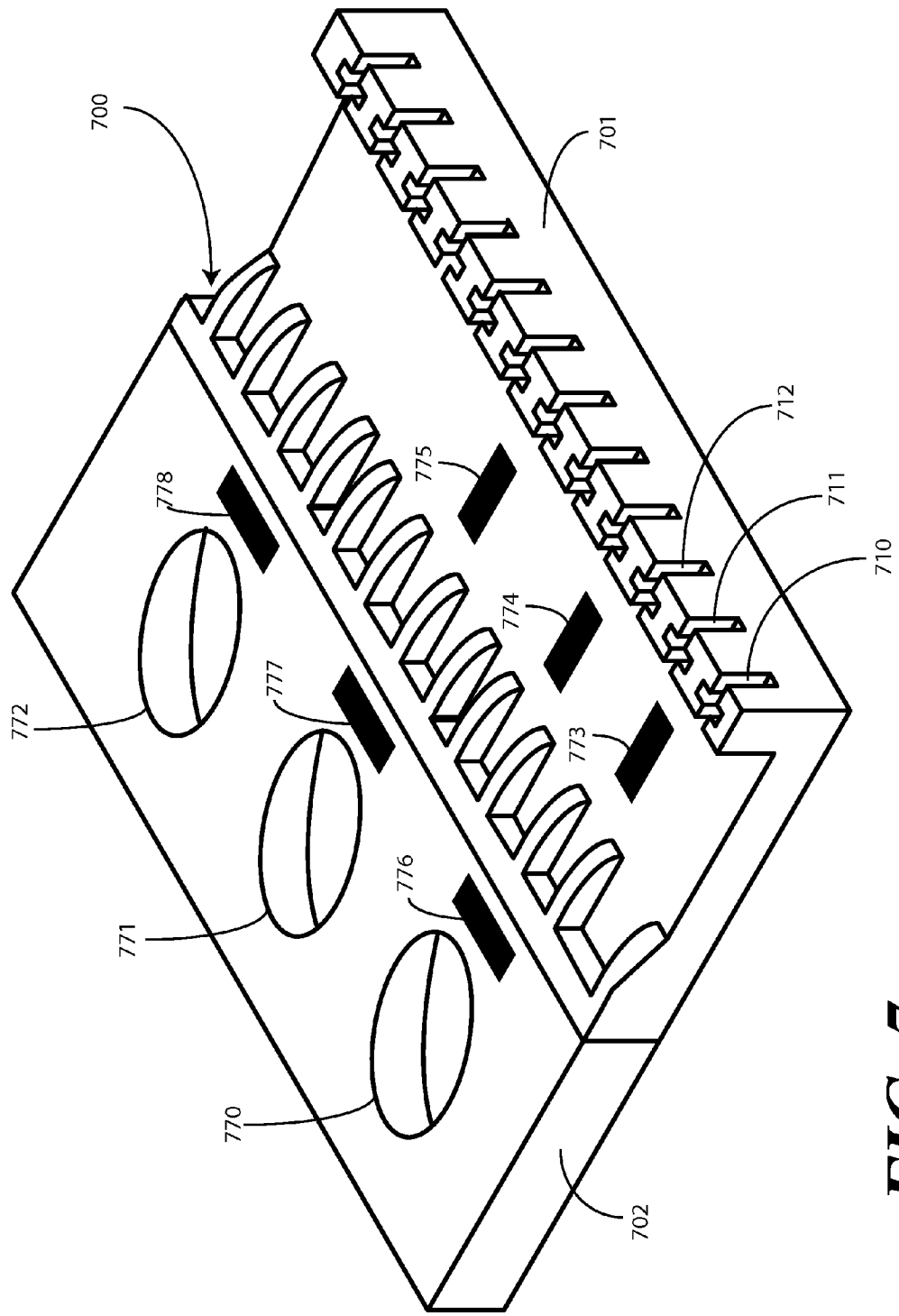
FIG. 7 illustrates one system for containing medical implements in accordance with embodiments of the invention.

Turning now to FIG. 7, illustrated therein is a system 700 for containing medical implements in accordance with embodiments of the invention. The system 700 includes a first medical tray 701 and a second medical tray 702. The first medical tray 701 includes one or more medical implement receivers 710,711,712. As with previous embodiments, each medical implement receiver 710,711,712 includes retention members having opposing faces that define an implement receiving recess. Each opposing face includes a slot extending into its retention member from the implement receiving recess.

The second medical tray 702, which is attached to the first medical tray 701, defines one or more cup holders 770,771,772. In one embodiment, the one or more cup holders 770,771,772 are configured to receive 30 milliliter cups. In another embodiment, the one or more cup holders 770,771,772 are configured to receive 60 milliliter cups. Of course, combinations of these, as well as cups of other volumetric dimensions, may also be used with the system 700 of FIG. 7.

In some medical procedures, a medical services provider will need to draw fluid from a container, such as a cup, with a syringe for injection into a drip bag. The system 700 of FIG. 7 is well suited for this task, in that syringes can be inserted into the medical implement receivers 710,711,712 as previously described, while cups containing the proper medications can be placed into the one or more cup holders 770,771,772.

In one embodiment, to aid in ensuring that the proper medication is drawn from the proper syringe, a mnemonic device can be incorporated into the system. For example, the mnemonic device can include a color-coding system where each medical implement receiver 710,711,712 is coded with a color 773,774,775. Correspondingly, each cup holder 770,771,772 can be coded with a corresponding color 776,777,778. In one embodiment, these colors can correspond on a one-to-one basis. For instance, colors 773 and 776 may be blue, while colors 774 and 777 are yellow, and so forth.

In one embodiment, the color-coding system can be incorporated into the system 700 with adhesive labels having the various colors thereon. In another embodiment, the color-coding system can be incorporated into the system 700 by other means, such as painting or printing. Where the first medical tray 701 and second medical tray 702 are manufactured from a configurable material such as a thermoplastic, the colors can be molded into the plastic or affixed thereto during a post-molding coating process.

As noted above, the first medical tray 701 and second medical tray 702 can be selectively detachable. For example adjoining sides of each medical tray may include mechanical connectors, hook and loop connectors, adhesive connectors, and so forth that allow the trays to be separated. Where the trays are separable, different trays could be coupled together depending upon with which medical procedure the trays will be used. A first color coding scheme may be used with a first procedure, while a second color coding scheme can be used with a second procedure, and so forth. Alternatively, the first medical tray 701 and second medical tray 702 may be permanently coupled together, or may comprise a unitary device.

Figure 8:
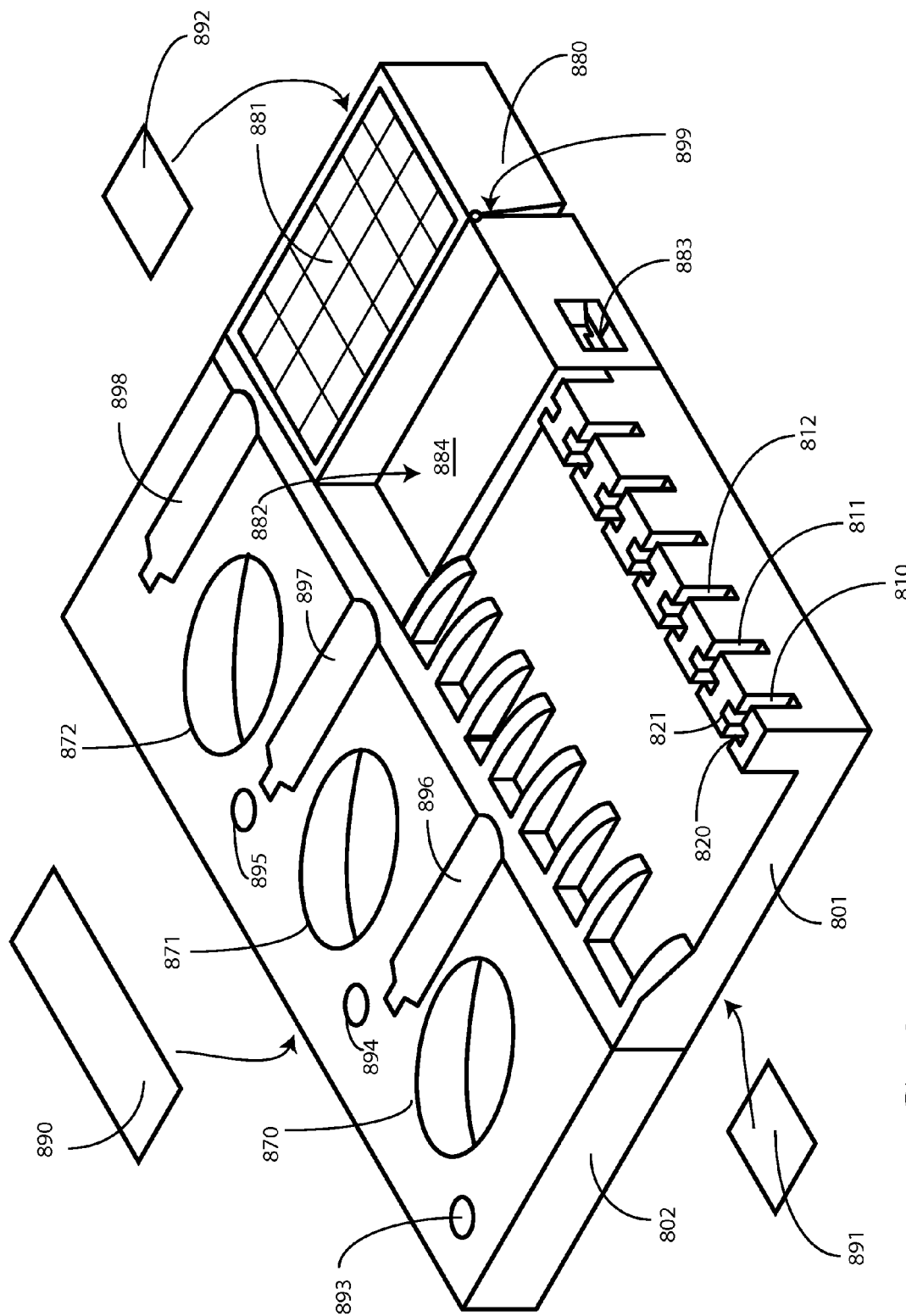
FIG. 8 illustrates another system for containing medical implements in accordance with embodiments of the invention.

Turning now to FIG. 8, illustrated therein is an alternate system 800 in accordance with embodiments of the invention. As with the system (700) of FIG. 7, the system 800 of FIG. 8 includes a first medical tray 801 having one or more medical implement receivers 810,811,812 and a second medical tray 802 defining one or more cup holders 871,872,873. The system 800 of FIG. 8 differs from the system (700) of FIG. 7 in that the first medical tray 801 has a shorter width than the second medical tray 802. Additionally, a third medical tray 880 is attached to each of the first medical tray 801 and the second medical tray 802. Note that the third medical try 880 could optionally be coupled to only one medical tray instead.

As with the embodiment of FIG. 3, in one embodiment of FIG. 8, each of the first medical tray 801, the second medical tray 802, and the third medical tray 880 can have a corresponding adhesive patch 890,891,892 or adhesive strip attached to the bottom of each tray. Such an adhesive patch 890,891,892 can be used to selectively adhere the trays to a surgical drape on a Mayo stand, or to a stand or table, to prevent slippage while in use In the embodiment of FIG. 8, the third medical tray comprises a needle containment receptacle 881. In the illustrative embodiment of FIG. 8, needle containment receptacle 881 comprises a foam block having a matrix printed thereon. A medical services provider can discard suture needles used in the procedure by sticking them into the foam. The matrix provides a numbering mnemonic device that allows a medical services provider to quickly account for all needles used in a given procedure. The needle containment receptacle 881 may be used for syringe needles as well. Note that the foam block of FIG. 8 can be configured as a matrix of foam strips instead. Alternatively, the foam block could comprise a magnet.

In this illustrative embodiment, the third medical tray 880 further includes a blade receptacle 882 for discarding scalpel blades. In one embodiment, a scalpel blade 883 can be inserted into a scalpel blade remover 883 that pops the blade from the handle. A magnetic surface 884 in the blade receptacle 882 retains the discarded blades within the third medical tray 880. An adhesive strip can be substituted for the magnet. An optional hinge 899 can be included between the blade receptacle 882 and the needle containment receptacle 881 so that the two can be pivotally rotated towards each other, upon detachment from the other trays, to safely and securely contain the sharp objects, i.e., the scalpel blades and suture needles, therein.

In practice, a medical services provider may place the system 800 of FIG. 8 on a stand during a medical procedure. Medicine cups could be placed within the cup holders 870,871,872 of the second medical tray 802, while the appropriate scalpels and syringes may be placed in the medical implement receivers 810,811,812. The slots 820,821 of the medical implement receivers 810,811,812 could then be used to remove and reattach syringe needle caps to the syringes. While the syringes were in use, the syringe needle cap could remain within the slots 820,821 so that it is ready for reattachment. Any suture needles, syringe needles, or scalpel blades could then be discarded in the third medical tray 880 after use.

Other optional features may be included as well. For example, syringe needle cap holders 893,894,895 can be provided. In such a configuration, when the syringes are in use, a medical services provider has the option of leaving the needle caps in the slots 820,821 of the medical implement receivers 810,811,812, or alternatively inserting them into the syringe needle cap holders 893,894,895. Additionally, syringe receiving recesses 896,897,898 can be provided to permit temporary resting places for syringes between medicine extractions from cups in the cup holders 870,871,872.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A holder for medical implements, comprising:
   a base member;
   at least one medical implement receiver, the at least one medical implement receiver comprising a pair of retention members extending from the base member, wherein opposing faces of each retention member define an implement receiving recess therebetween, each retention member comprising a slot extending into each retention member from a face disposed along the implement receiving recess; and
   a mechanical stop wall extending from the base member, separated from the at least one medical implement receiver by at least a portion of a width of the base member;
   wherein each retention member is configured to receive either a first medical implement or a second medical implement, wherein the first medical implement and the second medical implement are different.

2. The holder of claim 1, wherein the slot is configured to receive a portion of a syringe needle cap rim.

3. The holder of claim 1, wherein the opposing faces are separated by a length of between 1.27 millimeters and 8.89 millimeters.

4. The holder of claim 2, wherein the face comprises a face portion extending from the slot towards an edge of the holder, wherein the face portion has a length configured to fit between the syringe needle cap rim and a Luer fitting on a syringe.

5. The holder of claim 2, wherein the slot has a width of between 0.75 millimeters and 1.5 millimeters, wherein a retention member height is between 1 centimeter and 2.1 centimeters.

6. The holder of claim 1, further comprising an adhesive patch coupled to a base of the holder.

7. The holder of claim 1, wherein the opposing faces are pliable and are configured as cantilever surfaces for retaining a medical implement when inserted into the implement receiving recess.

8. The holder of claim 1, further comprising one or more separating walls extending from the mechanical stop wall towards the at least one medical implement receiver along a portion of a width of the base member.

9. A medical tray configured to hold syringe caps and scalpels, comprising:
   a base member having a raised rim about at least a portion of the base member;
   one or more medical implement receivers extending from the base member, each medical implement receiver comprising a pair of retention members having opposing faces that define an implement receiving recess, each opposing face comprising a slot extending into each retention member; and
   a lid configured to cover an area disposed at least between the raised rim and the one or more medical implement receivers.

10. The medical tray of claim 9, wherein the lid is coupled to the medical tray by a hinge.

11. The medical tray of claim 9, wherein the lid is selectively detachable from the medical tray.

* * * * *